US008685455B2

(12) United States Patent
Yamada et al.

(10) Patent No.: US 8,685,455 B2
(45) Date of Patent: Apr. 1, 2014

(54) OIL-IN-WATER EMULSIONS CONTAINING LIGNAN-CLASS COMPOUNDS AND COMPOSITIONS CONTAINING THE SAME (75) Inventors: Daisuke Yamada, Osaka (JP); Mineko Kato, Osaka (JP); Yoshiko Ono, Osaka (JP); Namino Tomimori, Osaka (JP); Toshihiro Nishiumi, Osaka (JP); Koichi Nakahara, Osaka (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 82 days.

(21) Appl. No.: 11/887,074

(22) PCT Filed: Mar. 31, 2006

(86) PCT No.: PCT/JP2006/306845
§ 371 (c)(1),
(2), (4) Date: Jan. 26, 2009

(87) PCT Pub. No.: WO2006/106926
PCT Pub. Date: Oct. 12, 2006

(65) Prior Publication Data
US 2009/0202643 A1 Aug. 13, 2009

(30) Foreign Application Priority Data

Mar. 31, 2005 (JP) .................... 2005-104946
Mar. 31, 2005 (JP) .................... 2005-105092

(51) Int. Cl.
*A61K 9/14* (2006.01)
(52) U.S. Cl.
USPC .................................................. 424/489
(58) Field of Classification Search
None
See application file for complete search history.

(56) References Cited

U.S. PATENT DOCUMENTS

| 4,427,694 | A | | 1/1984 | Benecke et al. |
| 5,180,588 | A | | 1/1993 | Shinmen et al. |
| 5,211,953 | A | | 5/1993 | Shinmen et al. |
| 5,270,335 | A | | 12/1993 | Akimoto et al. |
| 5,336,496 | A | | 8/1994 | Akimoto et al. |
| 5,364,632 | A | * | 11/1994 | Benita et al. .................. 424/450 |
| 5,438,041 | A | | 8/1995 | Zheng et al. |
| 5,637,610 | A | * | 6/1997 | Nakabayashi et al. ........ 514/458 |
| 6,150,425 | A | | 11/2000 | Sekine et al. |
| 2004/0033202 | A1 | | 2/2004 | Cooper et al. |
| 2004/0142040 | A1 | | 7/2004 | Dong et al. |
| 2006/0058376 | A1 | | 3/2006 | Maritani et al. |
| 2006/0073176 | A1 | * | 4/2006 | Segawa et al. ................. 424/401 |
| 2007/0085058 | A1 | * | 4/2007 | Mora-Gutierrez et al. .......... 252/400.21 |
| 2007/0166255 | A1 | | 7/2007 | Gupta |

FOREIGN PATENT DOCUMENTS

| AU | 2005320579 B2 | 7/2006 |
| CN | 1568938 | 1/2005 |
| CN | 1208041 C | 6/2005 |
| DE | 24 51 568 A1 | 5/1975 |
| EP | 0 215 313 A2 | 3/1987 |
| EP | 0 409 654 A2 | 1/1991 |
| EP | 0988858 A1 | 3/2000 |
| GB | 1 488 522 | 10/1977 |
| JP | 63-44842 | 2/1988 |
| JP | 63-44843 | 2/1988 |
| JP | 02138120 A | 5/1990 |
| JP | 2-200145 | 8/1990 |
| JP | 03-053866 | 3/1991 |
| JP | 3070611 A | 3/1991 |
| JP | 03153625 A | 7/1991 |
| JP | 04-290822 | 10/1992 |
| JP | 5-43458 | 2/1993 |
| JP | 5-051388 | 3/1993 |
| JP | 05130843 | 5/1993 |
| JP | 06227977 A | 8/1994 |
| JP | 07313055 | 12/1995 |
| JP | 08317775 A | 12/1996 |
| JP | 09-157159 | 6/1997 |
| JP | 09-315955 | 9/1997 |
| JP | 10067656 A | 3/1998 |
| JP | 3001589 | 1/2000 |
| JP | 3075358 | 8/2000 |
| JP | 3075360 | 8/2000 |
| JP | 3124062 | 1/2001 |
| JP | 3183664 | 7/2001 |
| JP | 3283274 | 5/2002 |
| JP | 2002322191 A | 11/2002 |

(Continued)

OTHER PUBLICATIONS

Supplementary European Search Report dated Jul. 14, 2009 issued in European Patent Application No. 06 73 0793.
Examiner's first report issued Jul. 19, 2010 in AU Application No. 2006231967.
International Search Report issued on Jun. 27, 2006 in International PCT Application No. PCT/JP2006/306845 filed Mar. 31, 2006.
Nami Yiyao ("Nano Medicine"), edited by Huibi Xu, pp. 104-106, Tsinghua University Press, 2004 (w/ partial English translation).

(Continued)

*Primary Examiner* — Brian Gulledge
*Assistant Examiner* — Snigdha Maewall
(74) *Attorney, Agent, or Firm* — Drinker Biddle & Reath LLP (57) ABSTRACT

An object of the present invention is to increase the rate at which lignan-class compounds are absorbed into the body, namely, to provide fast-acting lignan-class compounds.
Provided is an oil-in-water emulsion which comprises a water phase and an oil phase comprising at least one kind of lignan-class compounds dissolved therein and being emulsified in the water phase, wherein the oil droplets which serve as a dispersion phase in the emulsion are made finer by high-speed agitation or other method so that their average particle size is 1000 nm or smaller, preferably 500 nm or smaller, and more preferably 300 nm or smaller, whereby the rate at which lignan-class compounds are absorbed into the body is improved to impart immediate action.

11 Claims, 7 Drawing Sheets

(56) References Cited

FOREIGN PATENT DOCUMENTS

| | | |
|---|---|---|
| JP | 2003286127 A | 10/2003 |
| JP | 2004097113 | 4/2004 |
| JP | 2004-196781 | 7/2004 |
| WO | WO 2004/000304 A | 12/2003 |
| WO | WO 2004/105749 | 9/2004 |

OTHER PUBLICATIONS

International Search Report mailed Jan. 15, 2008 in PCT/JP2007/069290 filed Oct. 2, 2007.

English Translation of CN 1568938.

Joscelyne et al., "Membrane emulsification—a literature review," Journal of Membrane Science, 169 (2000) 107-117.

* cited by examiner

OIL-IN-WATER EMULSIONS CONTAINING LIGNAN-CLASS COMPOUNDS AND COMPOSITIONS CONTAINING THE SAME

CROSS REFERENCE TO RELATED APPLICATIONS

This application is the National Stage of International Application No. PCT/JP2006/306845 filed Mar. 31, 2006, and claims benefit of Japanese Application No. 104946/2005 filed Mar. 31, 2005 and Japanese Application No. 105092/2005 filed Mar. 31, 2005, all of which are herein incorporated by reference in their entirety.

TECHNICAL FIELD

The present invention relates to oil-in-water emulsions containing lignan-class compounds and compositions containing the same. More particularly, the present invention relates to compositions having improved rates at which lignan-class compounds are absorbed in the body.

BACKGROUND ART

Lignan-class compounds have been reported to have a variety of in vivo actions. For example, U.S. Pat. No. 4,427,694 discloses the effectiveness of sesamin in alleviating the symptoms of alcohol intoxication and/or alcohol or tobacco withdrawal; and JP 2-138120 A discloses the effectiveness of sesaminol and episesaminol in the treatment and prevention of allergosis such as bronchial asthma. The assignees of the subject application also confirmed various physiological actions of lignan-class compounds and, to date, they have revealed such effects as the blood cholesterol lowering action (Japanese Patent No. 3001589), the action of inhibiting $\Delta^5$-unsauration enzymes (Japanese Patent No. 3070611), the action of improving hepatic functions (Japanese Patent No. 3075358), cholesterol depression (Japanese Patent 3075360), the action of preventing sickness from drinking (Japanese Patent No. 3124062), the action of inhibiting the metabolism of cholesterol and bile acid, as well as lowering cholesterol (Japanese Patent No. 3283274), the carcinogenesis suppressing action (Japanese Patent No. 3183664), the breast cancer suppressing action (JP 05-043458 A), as well as the action of suppressing the generation of lipid peroxides (JP 05-051388 A), and the action of scavenging active oxygen (JP 06-227977 A).

Some of these effects of lignan-class compounds are preferably exhibited gradually over a prolonged period but there are also some effects that are desirably exhibited soon after they are ingested. For example, the effectiveness in preventing sickness from drinking and the effectiveness in scavenging active oxygen are desirably of quick action.

However, lignan-class compounds are hardly soluble in water and, what is more; they dissolve to only some extent in organic solvents that can be used in medicaments or foods. Such fat-soluble substances have the problem of not being easily absorbed in the living body. As a method of improving the bodily absorption of fat-soluble substances, it has been proposed to make finer micelles of fat-soluble substances (render them in finer particles). This exploits a nature of fat-soluble substances in that, the smaller the size of their particles, the more advantageous they are in terms of absorption by the digestive tract. To give a specific example, JP 2004-196781 A discloses a coenzyme Q10 containing water-soluble composition that comprises coenzyme Q10, a specified polyglycerin, fatty acid monoester, etc. and which is markedly improved in bodily absorption by adjusting the average particle size to 110 nm or smaller. As another example, JP 9-157159 A discloses a carotinoids containing composition comprising an oil phase that has carotinoids dissolved in oil or fat and that is emulsified in a water phase containing a polyglycerin fatty acid ester, lecithin and a polyhydric alcohol and which has the bodily absorption of a sparingly soluble substance, carotenoid, improved by adjusting the average particle size of the oil phase to 100 nm or smaller.

As described above, it is known to improve the absorbability (i.e., total amount of absorption) into the body of fat-soluble substances by making finer micelles of the substances (rendering them in finer particles). However, the above-mentioned documents do not either suggest or disclose anything about the rate at which the fat-soluble substances are absorbed into the body.

Patent Document 1: U.S. Pat. No. 4,427,694
Patent Document 2: JP 2-138120 A
Patent Document 3: Japanese Patent No. 3001589
Patent Document 4: Japanese Patent No. 3070611
Patent Document 5: Japanese Patent No. 3075358
Patent Document 6: Japanese Patent No. 3075360
Patent Document 7: Japanese Patent No. 3124062
Patent Document 8: Japanese Patent No. 3283274
Patent Document 9: Japanese Patent No. 3183664 (JP 04-159221 A)
Patent Document 10: JP 05-043458 A
Patent Document 11: JP 05-051388 A
Patent Document 12: JP 06-227977 A
Patent Document 13: JP 2004-196781 A
Patent Document 14: JP 9-157159 A

DISCLOSURE OF THE INVENTION

Problems to be Solved by the Invention

The present inventors were led to the idea that if the rate of bodily absorption of lignan-class compounds could be increased, namely, if they could obtain fast-acting lignan-class compounds, some of the actions of lignan-class compounds would be exhibited more efficiently than they had been before. To state specifically, the idea is that if lignan-class compounds that are rendered to have a faster bodily absorption rate are ingested either immediately before or after drinking an alcoholic beverage, their action of preventing sickness from drinking can be exhibited efficiently. Alternatively, the idea states that if lignan-class compounds that have a faster bodily absorption rate are ingested immediately before taking exercise, the active oxygen that is generated in the body during exercise can be scavenged efficiently.

Therefore, an object of the present invention is to increase the rate at which lignan-class compounds are absorbed into the body, namely, to provide fast-acting lignan-class compounds.

Means for Solving the Problems

The present inventors conducted intensive studies in order to attain the above-stated object; as a result, it was surprisingly found that when a lignan-class compound containing a composition comprising an oil-in-water emulsion that had been prepared by emulsifying in a water phase an oil phase containing at least one kind of lignan-class compounds dissolved therein was administered orally, the lignan-class compound could be absorbed into the body at a markedly higher rate than when it was administered orally when dissolved in fat or oil; the present invention has been accomplished on the basis of that finding.

Thus, the present invention provides an oil-in-water emulsion comprising a water phase and an oil phase emulsified in the water phase, wherein the oil phase comprises at least one kind of lignan-class compounds dissolved in the oil phase. The oil droplets which serve as a dispersion phase in the emulsion are not limited in any particular way so long as when the emulsion containing at least one kind of lignan-class compounds in a clinically effective amount is administered orally on an empty stomach, the lignan-class compound can be absorbed at such a rate that the time to reach maximum blood concentration (Tmax) is within 5 hours, preferably within 2.5 hours, more preferably within 2.0 hours. According to the studies made by the present inventors, such a satisfactory absorption was observed in each of the emulsions having average particle sizes of 100 nm, 130 nm, and 250 nm.

The present invention also provides a lignan-class compound containing composition that enables a lignan-class compound to be absorbed at such a rate that the time to reach maximum blood concentration (Tmax) is within 5 hours, preferably within 2.5 hours, more preferably within 2.0 hours, after oral administration. The present invention also provides a process for producing the composition. This composition can be produced by a process comprising the following steps:
1) dissolving at least one of lignan-class compounds in oil or fat to prepare a lignan-class compound dissolving liquid which serves as an oil phase;
2) emulsifying the lignan-class compound dissolving liquid in a water phase to form an oil-in-water emulsion; and
3) further emulsifying the lignan-class compound dissolving liquid until the oil droplets in the emulsion are reduced to an average particle size of 1000 nm (preferably 500 nm) or smaller.

Effect of the Invention

If lignan-class compounds are administered orally according to the present invention, the time to reach maximum blood concentration (Tmax) is shortened considerably and the maximum blood concentration (Cmax) enhanced as compared to the case where they are simply dissolved in fat or oil and administered under the same conditions.

Therefore, by ingesting lignan-class compounds as an antioxidant immediately before taking exercise according to the present invention, the active oxygen that is generated during exercise can be scavenged efficiently. In addition, by taking them as an alcohol metabolism improving agent either immediately before or after drinking an alcoholic beverage, it is possible to prevent sickness from drinking.

The composition of the present invention can of course be used in such forms as tablets or capsules; in addition, having superior dispersion stability, the composition can also be used in the form of a food or beverage, in particular, a health drink.

BEST MODE FOR CARRYING OUT THE INVENTION

Lignan-Class Compounds

The lignan-class compounds to be used in the present invention include sesamin, sesaminol, episesamin, episesaminol, sesamolin, 2-(3,4-methylenedioxyphenyl)-6-(3-methoxy-4-hydroxyphenyl)-3,7-dioxabicyclo[3,3,0]octane, 2,6-bis-(3-methoxy-4-hydroxyphenyl)-3,7-dioxabicyclo[3,3,0]octane, and 2-(3,4-methylenedioxyphenyl)-6-(3-methoxy-4-hydroxyphenoxy)-3,7-dioxabicyclo[3,3,0]octane; these compounds may be used either alone or in admixture.

The above-mentioned lignan-class compounds are in no way limited with respect to their form, the process for their production, and so forth. For example, one may use the extract from sesame oil as obtained by a known method (such as the method comprising adding hot methanol to the sesame oil for extraction, removing the methanol from the extract, then adding acetone to the residue for extraction (this method is described in JP 4-9331 A)) (the extract containing a high proportion of lignan-class compounds or being optionally purified); if desired, commercial sesame oil (in liquid form) can also be used. However, if sesame oil is used, its characteristic flavor may sometimes be evaluated as being unfavorable from an organoleptic viewpoint, so it is preferred to use the tasteless and odorless extract from sesame oil that contains a high proportion of lignan-class compounds or the purified product of such extract. Another problem with the use of sesame oil is that the content of lignan-class compounds is so low that if one attempts to incorporate a preferred amount of lignan-class compounds, the composition to be formulated that contains the lignan-class compound containing oil-in-water emulsion needs to be ingested in an excessive amount that might cause some inconvenience in ingestion. Therefore, from the additional viewpoint of the need to ingest only a small amount of the composition, it is preferred to use the extract from sesame oil that contains a high proportion of lignan-class compounds or a pure form of lignan-class compounds that have been isolated and purified. It should be noted here that the extract from sesame seeds and the like that contain a high proportion of lignan-class compounds has the pleasant aroma of sesame, so if it is used in food or beverage for animals according to the present invention, the aroma of sesame can be imparted to it.

Lignan-class compounds can also be obtained by synthesis. Exemplary methods include the method of Beroza et al. for sesamin and episesamin (J. Am. Chem. Soc., 78, 1242 (1956)), as well as the method of Freundenberg et al. for pinoresinol (Chem. Ber., 86, 1157 (1953)) and the method of Freundenberg et al. for syringaresinol (Chem. Ber., 88, 16 (1955)).

Further, the lignan-class compounds can be used in the form of glycosides and, in addition, these can be used either alone or in suitable combinations as components of the composition.

Lignan-Class Compound Containing Emulsion

According to the present invention, there is provided an emulsion comprising a lignan-class compound. As used herein, the term lignan-class compound in emulsion refers to an oil-in-water emulsion in which fat or oil (to form an oil phase) comprising a lignan-class compound dissolved therein is dispersed in a water phase such as water.

The term "oil phase" as used herein means a lignan-class compound dissolving liquid which has lignan-class compounds dissolved in oil or fat. Specific examples include not only sesame oil and a sesame extract containing a high proportion of lignan-class compounds that remain dissolved in sesame oil (sesame oil concentrate) but also a sesame extract, as well as a product prepared by dissolving a powdered form (solid forms) of lignan-class compounds, such as refined lignan-class compounds and the like, in fat or oil. The fat or oil in which lignan-class compounds are to be dissolved is not limited in any particular way and those which can be added to foods or pharmaceuticals and can dissolve lignan-class compounds may be used either alone or in admixture of two or more species. Specific examples include: natural oils and fats such as almond oil, safflower oil, apricot kernel oil, avocado oil, evening primrose oil, wheat germ oil, corn oil, sunflower oil, safflower oil, walnut oil, olive oil, castor oil, kukui nut oil, grape seed oil, cocoa butter, coconut oil, soybean oil, rapeseed oil, peanut oil, rice oil, sesame oil, palm kernel oil, palm oil, jojoba oil, macadamia nut oil, shea butter, mango butter, kokum butter, whale oil, sardine oil, and squid oil; and synthetic oils or fats such as margarine; while fat or oil that contain as a main ingredient the diacylglycerol contained in the above-mentioned olive oil and the like, as well as fat or oil that contain as a main ingredient the middle-chain fatty acid triglyceride (MCT) contained in palm kernel oil and the like can also be used, those oils or fats which contain large amounts of saturated fatty acids are particularly preferred since they are not readily oxidized. In addition, not only fats or oils that are liquid at ordinary temperatures but also those which are mixed with semi-solid or solid lard, tallow, hydrogenated fish oil, margarine, shortening, and the like may be used. Since the lignan-class compounds and the extract that contains a high proportion of lignan-class compounds are the active ingredients that were initially present in edible fats or oils and their extract, these can be readily added to fats or oils and by simply mixing them at ordinary temperatures, the lignan-class compounds can be dissolved; however, depending on the need, they may be heated for dissolution or otherwise treated.

The "water phase" as used herein is not limited in any particular way as long as it is an aqueous medium; examples include not only water and aqueous solutions but also a variety of aqueous drinks such as common drinks like juice drinks, carbonated drinks, cow's milk, soymilk, cereal drinks, coffee, green tea, etc., and alcoholic beverages.

If desired, a solubilizing agent may be added to the water phase for the purpose of increasing the percent content of the oil phase. Examples of such solubilizing agent include propylene glycol, ethanol, mono- or di-saccharides, and sugar alcohols (e.g. sorbitol, xylitol, and mannitol).

To prepare the lignan-class compound containing emulsion of the present invention, liquid in which a lignan-class compound is dissolved (oil phase) is first prepared. As already mentioned, a sesame oil or the like may be used as the liquid, alternatively, the liquid may be prepared by adding a powdered form of lignan-class compound to a solvent oil or fat, mixing the mixture, and fully dissolving the powdered form to the solvent while agitating the mixture while heating. The blending ratio between the lignan-class compound and the fat or oil varies with the type of the lignan-class compound and the fat, or oil that serves as a solvent and it can be set appropriately in consideration of this fact. The assignees of the subject application have discovered that two lignan-class compounds, sesamin and episesamin, and a mixture thereof had different solubilities in different fats or oils (see Table 1).

TABLE 1

Solubilities (%) of Sesamin, Episesamin, and Their Mixture in Various Oils or Fats

| Oil or Fat | Wheat germ oil | Olive oil | MCT-1[*1] | MCT-2[*2] | DG[*3] |
|---|---|---|---|---|---|
| Mixture[*4] | 2.0 | 1.5 | 7.0 | 6.5 | 1.5 |
| Sesamin | 0.75 | 0.75 | 4.0 | 2.0 | 1.25 |
| Episesamin | 0.75 | 0.5 | 2.5 | 2.5 | 1.0 |

[*1]MCT-1 . . . ACTOR M-1 of RIKEN VITAMIN CO., LTD. (middle-chain fatty acid triglycerides at C8:C12 = 1:1)
[*2]MCT-2 . . . ACTOR M-2 of RIKEN VITAMIN CO., LTD. (C8 middle-chain fatty acid triglyceride)
[*3]diacylglycerol . . . ECONA COOKING OIL of Kao Corporation
[*4]mixture . . . sesamin/episesamin = 51.1:48.2

As is clear from Table 1, lignan-class compounds are fully dissolved when the blending ratio (by weight) between lignan-class compound and oil or fat is such that the lignan-class compound to solvent ratio is about 1:15-2000, preferably about 1:15-100.

By mixing this oil phase with a water phase and homogenizing the mixture, there is obtained an oil-in-water emulsion having the oil droplets dispersed in the water.

The mixing ratio (by weight) between the oil phase and the water phase can be appropriately set in order to incorporate lignan-class compounds at desired concentrations; for example, the oil to water phase ratio can be set at 1:2-100, preferably at 1:3-50.

The physical techniques for achieving homogenization are not limited in any way and may be exemplified by such apparatuses as an agitating emulsifier, a high-pressure homogenizer, an ultrasonic emulsifier, an ultra-mixer, and a colloid mill.

According to the review by the present inventors, if no homogeneous emulsion is formed, or if the dispersion stability of oil droplets in emulsion is poor, absorbability into the body (i.e., total amount of absorption, which may be referred to herein as "the amount of absorption" or "AUC") may sometimes decrease. In order to obtain a homogeneous emulsion, a surfactant may advantageously be added to the water phase and/or oil phase of the emulsion. Surfactants may be selected as appropriate for the types and amounts of lignan-class compounds, as well as oils and fats; examples include glycerin fatty acid esters, sucrose fatty acid esters, sucrose acetate isobutyrate, sorbitan fatty acid esters, propylene glycol fatty acid esters, calcium stearyl lactate, soybean saponin, lecithin, wheat protein digest, gelatin, carboxymethylcellulose, carboxymethylcellulose sodium, gum arabic, xanthan gum, arabinogalactan, dextrin, casein, and casein sodium; these surfactants may be used either alone or in admixture. If the lignan-class compound is sesamin and/or episesamin, lecithin or its derivatives are preferred as surfactants, and lysolecithin is particularly preferred. Lysolecithin is one of water-soluble lecithin derivatives and also known as lysophospholipid, 1-monoacylglycerophospholipid, enzyme-decomposed lecithin, enzyme-modified lecithin, lysophosphatidylcholine, or mono-O-acyl-3-phosphorylcholine, with its chemical name being 1-acyl-sn-glycero-3-phosphatidylcholine. Lysolecithin can be produced by treating lecithin with phospholipase $A_2$ or the like. Processes for producing lysolecithin are disclosed in, for example, JP 62-279832 A, JP 63-44893 A, JP 63-279753 A, etc. and it is commercially available under trade names such as Lecinol and Sunlecithin. Lysolecithin need not be a pure product. Higher levels of purities are preferred but as long as a purity of at least 30% is assured, other impurities can be contained without any problem.

Lecithin is also preferred for the reason that it is a natural emulsifier obtained from soybean or egg yolk. In addition, enzyme-decomposed lecithin which is produced by hydrolyzing ester bonds in a fatty acid to increase the number of hydroxyl groups is also preferred for the reason that it has a very high O/W emulsifying power due to the increased hydrophilicity and that it is water-soluble and has high resistance to acid, salt and heat.

If a surfactant is to be used, the blending ratio (by weight) between the lignan-class compound containing oil phase and the surfactant may be 1:0.05-10, preferably 1:0.1-5.

In addition, it is generally known that with the decreasing particle size, the surface area increases, thus contributing to increased electrostatic stability and improved dispersion stability. Therefore, in order to obtain a homogeneous emulsion, it is also effective to reduce the particle size of oil droplets that compose the dispersion phase (i.e., render them finer). Specifically, the average particle size of oil droplets may be adjusted to 1000 nm or less, preferably 500 nm or less, more preferably 300 nm or less. At 300 nm or less, the emulsion can be left to stand at room temperature for 2 days without causing segregation of the oil phase, thus showing satisfactory dispersion stability. According to the study by the present inventors, it was found that the particle size of oil droplets decreased in a specific way when MCT was used as an oil or fat. Stated more specifically, compared to the case where sesamin and episesamin containing emulsions that were produced using olive oil as an oil or fat had average particle sizes of 862.3 nm, 157.3 nm, and 172.9 nm, sesamin and episesamin containing emulsions that were produced under the same conditions except that MCT was used as an oil or fat had average particle sizes of 277.7 nm, 81.5 nm, and 95.9 nm, respectively. Therefore, if it is desired to produce oil droplets of lignans in small enough size, particularly 100 nm and less, MCT is advantageously selected as an oil or fat. As MCT, the one which is present as a component of vegetable oils or fats such as palm oil, coconut oil and babassu oil can be used; alternatively, artificially synthesized MCTs may also be used.

The oil-in-water emulsion of the present invention can be produced by mixing the oil and water phases and homogenizing the mixture. In order to produce an emulsion containing the above-described fine oil droplets with average particle sizes of 1000 nm or less, preferably 500 nm or less, more preferably 300 nm or less, preliminary emulsification that consists of mixing the oil and water phases may be followed by a means of further emulsification (main emulsification) until the average particle size of the oil droplets come within the above-mentioned ranges. The emulsifying means that can be employed is not limited in any particular way as long as it is capable of high-speed agitation and specific examples include those which were already mentioned for the homogenizing treatment and are exemplified by such apparatuses as an agitating emulsifier, a high-pressure homogenizer, an ultrasonic emulsifier, an ultra-mixer, and a colloid mill. Agitation conditions may be set as appropriate for the type and shape of the apparatus used, as well as the properties and quantity of the object to be treated (the mixture of oil and water phases) and they are typically about 10-30 minutes at 5000-30000 rpm, preferably at 6000-20000 rpm.

Aside from the above-mentioned lignan-class compound, oil or fat, water-based solvent, and the surfactant, an antioxidant such as vitamin C, vitamin E, d-α-tocopherol, ellagic acid, erythorbic acid, sodium erythorbate, ethylenediaminetetraacetic acid disodium salt, dibutyl hydroxytoluene, sodium L-ascorbate, and pherol may be mixed into the lignan-class compound containing emulsion of the present invention for the purpose of preventing oxidation. If necessary, a sweetener, a seasoning, a sour agent, a pH modifier and the like may be added.

Uses

The present invention contributes to improving the absorbability of lignan-class compounds in the living body. Hence, the oil-in-water emulsion of the present invention can be used in the form of various food compositions or oral pharmaceutical compositions which can benefit from the absorption rate of lignan-class compounds. The food compositions of the present invention also include those in the form of drinks. The food compositions of the present invention can be formulated as food with nutrient function claims, food for specified health use, health food, nutritional supplement, health drink, softgel, etc.

The ratio (by weight) at which the oil-in-water emulsion of the present invention is blended in the food composition or oral pharmaceutical composition can be appropriately set for the purpose of incorporating the lignan-class compound at a desired concentration in a desired amount and it may range from about 1 to 100 wt %. In addition, the food composition or oral pharmaceutical composition of the present invention may use a variety of acceptable additives, such as excipient, binder, disintegrant, lubricant, coating agent, suspending agent, emulsifier, stabilizer, preservative, and buffer.

In the pharmaceutical composition of the present invention, the amount of the lignan-class compound as the active ingredient, the duration of its administration, and the interval between administrations can be set as appropriate for the specific object, symptom, the age and body weight of the subject to be treated, and other factors.

The subject to which may be applied the food composition or oral pharmaceutical composition of the present invention is humans or animals. The term animals refers to industrial animals, pets, and laboratory animals; specifically, the term industrial animals refers to animals that are bred for industrial purposes and they include farm animals such as cattle, horse, swine, goat, sheep, etc., poultry such as chicken, duck, quail, turkey, ostrich, etc., and fishes such as adult yellowtail, young yellowtail, red sea bream, common horse mackerel, carp, rainbow trout, eel, etc; the term pets refers to so-called pet animals or companion animals such as dog, cat, marmoset, little bird, hamster, goldfish, etc.; the term laboratory animals refers to rat, guinea pig, beagle, miniature pig, rhesus monkey, crab-eating monkey, and other animals that are subjected to research in such fields as medicine, biology, agronomy, pharmacy, etc.

Method of Evaluation

If lignan-class compounds are administered orally according to the present invention, the time to reach maximum blood concentration (Tmax) is shortened considerably and the maximum blood concentration (Cmax) is enhanced as compared to the case where they are simply dissolved in fat or oil and administered under the same conditions. Such an improvement in absorbability into the body can be evaluated by measuring the level of lignan-class compounds in blood over time.

The concentration of lignan-class compounds in blood can be determined by the following procedure: blood is collected and subjected to a centrifugal operation to obtain a plasma sample, to which is added an internal standard (e.g., eudesmine produced by Funakoshi Corporation); thereafter, the sample is extracted with a solid-phase extracting polymer packing agent (e.g., Oasis HLB produced by Waters Corporation) and the liquid extract is concentrated under vacuum; the concentrate is then suspended in methanol, passed through a filter, and subjected to LC-MS/MS for quantification of the lignan-class compounds.

In the case where a plurality of lignan-class compounds is used, the total sum of their blood levels may be employed to determine Cmax and Tmax for evaluation.

It should be noted here that the term average particle size as used herein means, except in special cases, the median size (the particle size corresponding to 50% on a plus-mesh distribution curve; sometimes referred to as a 50% particle size) and this can be known by the method of light scattering, particle size distribution measurement. The method of dynamic, light scattering, particle size distribution measurement may also be adopted.

EXAMPLES

The present invention is described more specifically by showing working examples and comparative examples below, but it should be understood that the present invention is by no means limited to the following working examples.

Example 1

Absorption Test-1

Samples

One gram of sesamin (product of TAKEMOTO OIL & FAT Co., Ltd.; sesamin/episesamin=51.1:48.2) was suspended in 50 g of olive oil that had been heated to 80° C. and the suspension was agitated for 20 minutes until the sesamin dissolved uniformly. The resulting solution was cooled to about 70° C. and poured while agitating, into an aqueous solution prepared by mixing and dissolving 25 g of enzyme-decomposed lecithin (SUNLECITHIN VA-1; product of Taiyo Kagaku Co., Ltd.; 33.3% active ingredient; obtained from soybean) in 1000 mL of water that had been heated to 70° C., and the mixture was emulsified at 6000 rpm for 15 minutes with Distromix (product of ATEC JAPAN Co., Ltd.). The emulsified liquid was held at 50-60° C. and processed with a high-speed agitating emulsifier (CLEAR MIX W-Motion, product of M Technique) for 40 minutes with the rotor part running at 20000 rpm and the screen part at 12500 rpm, whereby a sesamin-containing, water-soluble emulsified composition (sesamin-containing, oil-in-water emulsion) was obtained (sample 1). The average particle size of the obtained sesamin-containing, oil-in-water emulsion was measured with the dynamic light scattering particle size distribution analyzer Model LB-550 of HORIBA, Ltd. and the result was 97.8 nm.

For comparison, 50 mg of sesamin (product of TAKEMOTO OIL & FAT Co., Ltd.; sesamin/episesamin=51.1:48.2) was suspended in 50 mL of olive oil that had been heated to 80° C. and the suspension was agitated for 20 minutes until the sesamin dissolved uniformly (comparative sample).

Sesamin's Bodily Absorption Test

SD (IGS) male rats (9-week old) were purchased from CHARLES RIVER LABORATORIES, JAPAN, INC. and acclimatized in the test environment for a week; the animals that were shown to have grown normally were subjected to the test. The rats that were fasted overnight were divided into two groups, each consisting of 4 animals, and using a stomach tube, they were orally administered with the sesamin-containing, oil-in-water emulsion as sample 1 or sesamin dissolved in olive oil as the comparative sample at a dose of 10 mg/10 mL/kg. At 1, 3, 5, 7, 9 and 25 hours after the start of administration, blood was withdrawn from the tail vein of each animal, collected into a heparinized blood collecting tube, and centrifuged (8000 rpm, 10 min) to obtain plasma samples. After adding an internal standard, the samples were extracted with Oasis HLB and the liquid extract was concentrated under vacuum; the concentrate was suspended in methanol, passed through a filter and subjected to LC-MS/MS to quantitate sesamin and its isomer, episesamin. According to the usual method, the amounts of sesamin and episesamin were determined from the ratio between the peak area of sesamin or episesamin and the peak area of the internal standard eudesmine (Funakoshi Corporation). The conditions for LC-MS/MS analysis are shown below.

(HPLC)

Column: Develosil C30-UG-5 (5 μm, 2.0 Φ×50 mm; product of NOMURA CHEMICAL CO., LTD.)

Mobile phase: A, distilled water; B, methanol; D, 100 mM ammonium acetate in water Flow rate: 0.25 mL/min Gradient: Linear gradient consisting of 2 minutes with 55% fluid B and 10% fluid D, followed by 3 minutes with fluid B changing from 55% to 60% but fluid D remaining at 10%, then 2 minutes with fluid B changing from 60% to 85% but fluid D remaining at 10%.

(MS/MS)

Measurement mode: Monitoring of selective reaction

Detection: episesamin (about 5.6 min of retention time); precursor ion, m/z=372 ([M+NH$_4$]+), generated ion, m/z=233.

: eudesmine (about 2.8 min of retention time); precursor ion, m/z=404 ([M+NH$_4$]$^+$), generated ion, m/z=249.

Ionizing method: ESI method

Figure 1:
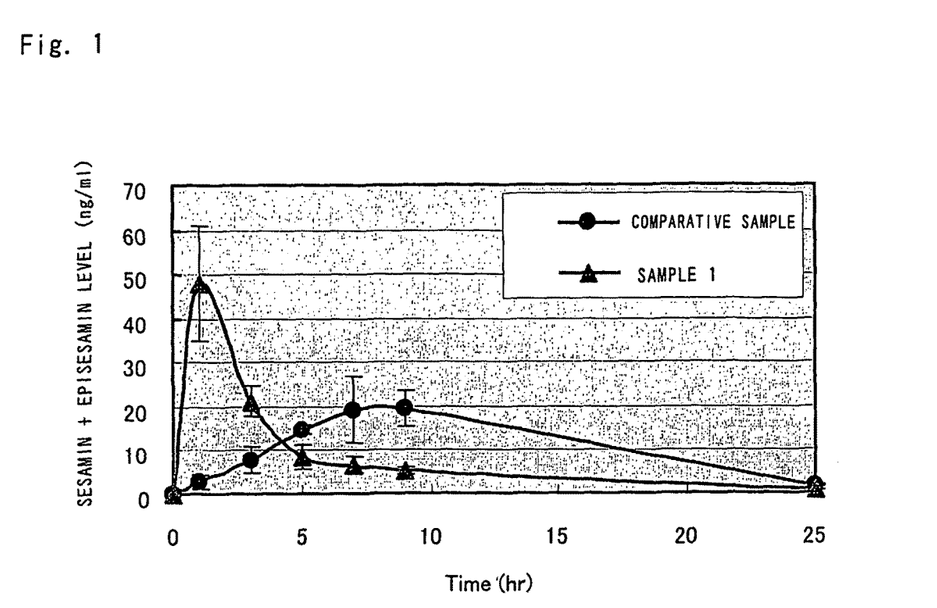
FIG. 1 is a graph showing the time course of the total sum of sesamin and episesamin levels (sesamin+episesamin level) in the blood of rats administered with the emulsion of the present invention (average particle size≈100 nm) or a comparative composition.
Figure 2:
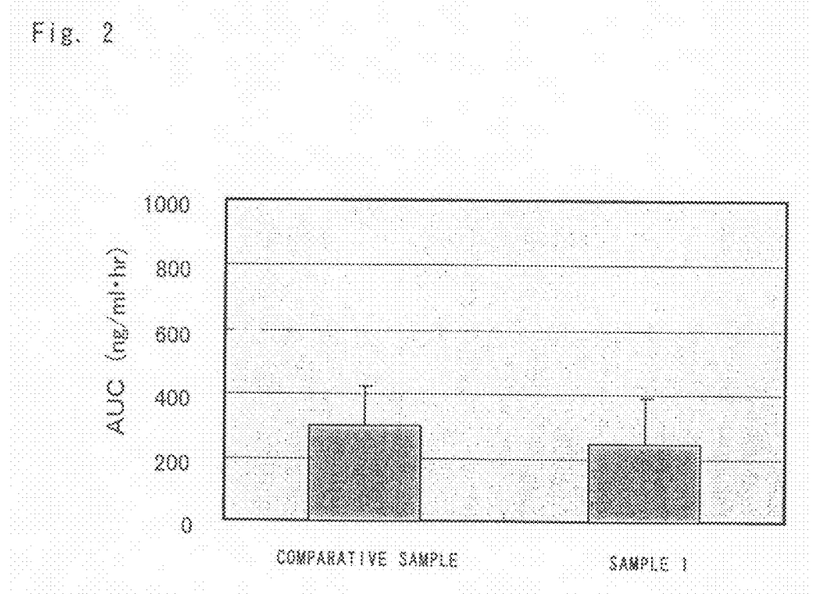
FIG. 2 is a graph showing the amount of bodily absorption (AUC) in rats administered with the emulsion of the present invention (average particle size≈100 nm) or a comparative composition.

FIG. 1 shows the time course of the total sum of sesamin and episesamin levels (sesamin+episesamin level) in blood. The maximum concentration of sesamin+episesamin in blood (Cmax) was 48 ng/mL in the sample 1 ingesting group but 20 ng/mL in the comparative sample ingesting group. The maximum concentration time of sesamin and episesamin (Tmax) was about one hour in the sample 1 ingesting group but about nine hours in the comparative sample ingesting group. Furthermore, the area under the blood concentration time curve (AUC) that represents the total amount of sesamin and episesamin absorbed by the body was determined from FIG. 1 and it was found that there was no difference in the amount of absorption (FIG. 2).

As shown in the foregoing, the group that ingested sample 1 (the aqueous solution containing finely ground lignan-class compounds) was no different in the amount of the sample absorbed by the body but there was improvement in the absorption rate, thus suggesting the immediate action of sample 1.

Example 2

Absorption Test-2

Samples

As in Example 1, a sesamin-containing, oil-in-water emulsion was prepared (sample 2). The production conditions were the same as in Example 1, except that the duration of emulsification with a high-speed agitating emulsifier was changed to 30 minutes. The average particle size of the oil droplets in this emulsion was 130 nm (as measured with the dynamic light scattering particle size distribution analyzer Model LB-550 of HORIBA, Ltd.).

Sesamin's Bodily Absorption Test

The test method was in accordance with Example 1. Rats fasted overnight were divided into two groups, each consisting of 6 animals, and using a stomach tube, they were orally administered with the sesamin-containing, oil-in-water emulsion as sample 2 (average particle size: 130 nm) or sesamin dissolved in olive oil as the comparative sample prepared in Example 1, at a dose of 10 mg/10 mL/kg.; the time course of blood levels was measured.

Figure 3:
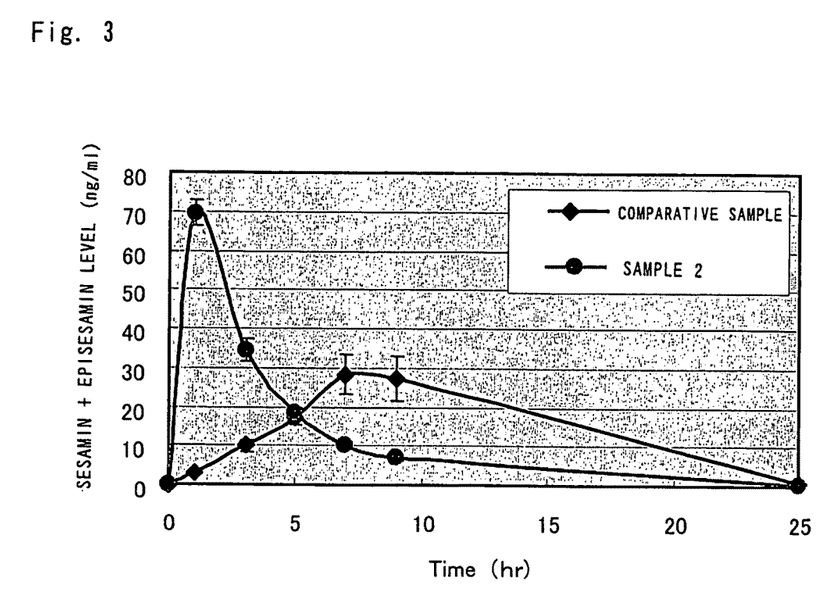
FIG. 3 is a graph showing the time course of the total sum of sesamin and episesamin levels (sesamin+episesamin level) in the blood of rats administered with the emulsion of the present invention (average particle size≈130 nm) or a comparative composition.
Figure 4:
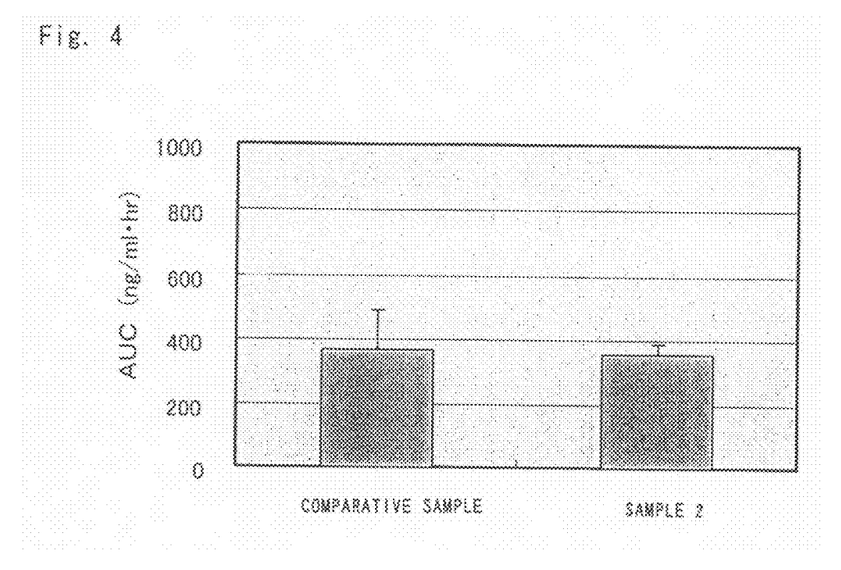
FIG. 4 is a graph showing the amount of bodily absorption (AUC) in rats administered with the emulsion of the present invention (average particle size≈130 nm) or a comparative composition.

FIG. 3 shows the time course of the total sum of sesamin and episesamin levels (sesamin+episesamin level) in blood. The Tmax was about seven hours in the comparative sample ingesting group but about one hour in the sample 2 ingesting group. The Cmax of sesamin+episesamin concentration in blood was 28 ng/mL in the comparative sample ingesting group but 69 ng/mL in the sample 2 ingesting group. In addition, the AUC was determined and it was found that there was no difference in the amount of absorption (FIG. 4). As shown in the foregoing, the group for the average particle size of 130 nm was no different in the amount of absorption but there was improvement in the absorption rate, thus suggesting the immediate action of sample 2.

Example 3

Absorption Test-3

Samples

As in Example 2, a sesamin-containing, oil-in-water emulsion was prepared (sample). The production conditions were the same as in Example 2, except that the emulsified liquid was held at 50-60° C. and processed with a high-speed agitating emulsifier (CLEAR MIX W-Motion, product of M Technique) with the rotor part running at 9000 rpm and the screen part at 6500 rpm. The average particle size of the oil droplets in this emulsion was 248.3 nm (as measured with the dynamic light scattering particle size distribution analyzer Model LB-550 of HORIBA, Ltd.).

Sesamin's Bodily Absorption Test

The test method was in accordance with Example 1. Rats fasted overnight were divided into two groups, each consisting of 6 animals, and using a stomach tube, they were orally administered with the sesamin-containing, oil-in-water emulsion as sample 3 (average particle size: 248.3 nm) or sesamin dissolved in olive oil as the comparative sample prepared in Example 1, at a dose of 10 mg/10 mL/kg.; the time course of blood levels was measured.

Figure 5:
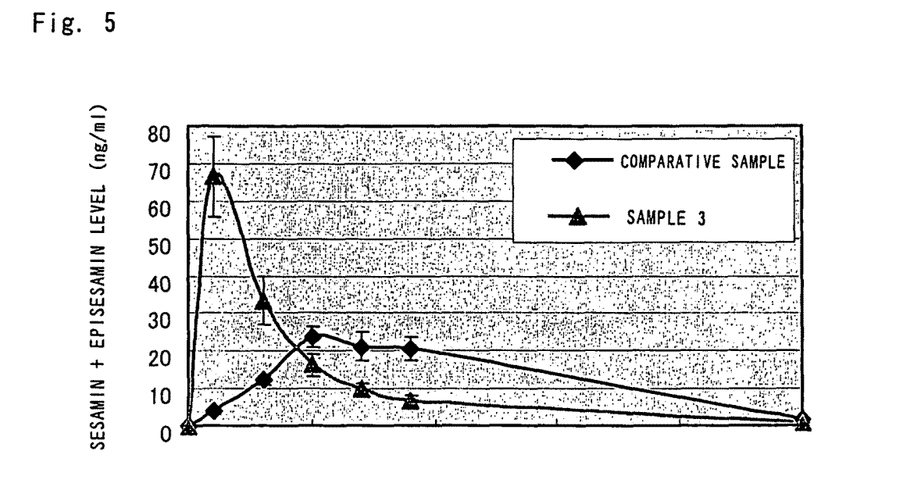
FIG. 5 is a graph showing the time course of the total sum of sesamin and episesamin levels (sesamin+episesamin level) in the blood of rats administered with the emulsion of the present invention (average particle size≈250 nm) or a comparative composition.
Figure 6:
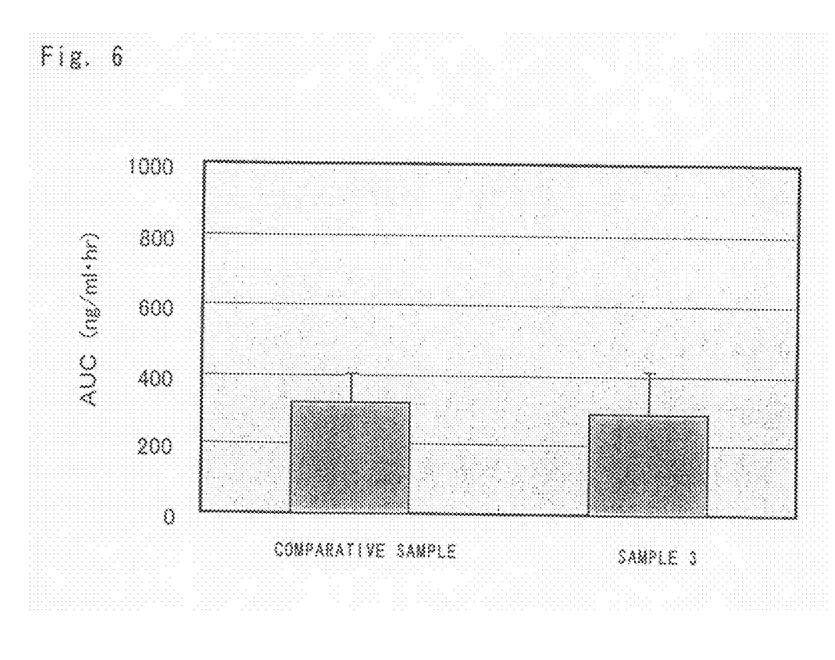
FIG. 6 is a graph showing the amount of bodily absorption (AUC) in rats administered with the emulsion of the present invention (average particle size≈250 nm) or a comparative composition.

FIG. 5 shows the time course of the total sum of sesamin and episesamin levels (sesamin+episesamin level) in blood. The Tmax was about five hours in the comparative sample ingesting group but about one hour in the sample 3 ingesting group. The Cmax of sesamin+episesamin level in blood was 24 ng/mL in the comparative sample ingesting group but 67 ng/mL in the sample 3 ingesting group. In addition, the AUC was determined from FIG. 4 and it was found that there was no difference in the amount of absorption (FIG. 6).

As shown in the foregoing, the group for the average particle size of 248.3 nm (≈250 nm) was also no different in the amount of absorption but there was improvement in the absorption rate, thus suggesting the immediate action of sample 3.

Example 4

Absorption Test-4

Sample 3 obtained in Example 3 (the sesamin-containing, oil-in-water emulsion with the average particle size of 248.3 nm) was left to stand for several months until the oil phase segregated in a very limited portion (as visually confirmed) (sample 4); this sample was subjected to a bodily absorption test as in Example 3.

Figure 7:
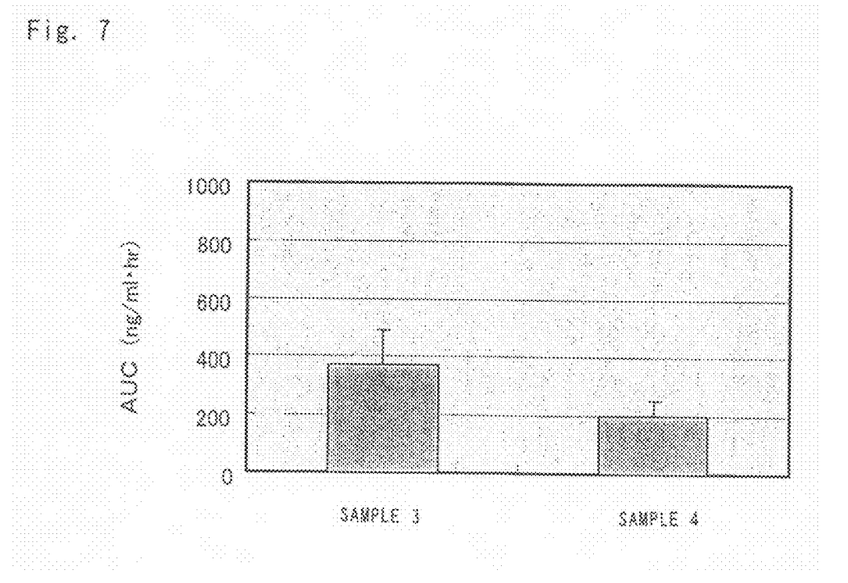
FIG. 7 is a graph showing the amount of bodily absorption (AUC) in rats administered with a homogeneous emulsified composition or a partially inhomogeneous emulsified composition, each comprising the emulsion of the present invention (average particle size≈250 nm).

Compared to sample 3, sample 4 was no different in Tmax but had the Cmax value lowered (data not shown). When the AUC was determined, the amount of absorption in the sample 4 ingesting group was found to have been lowered to about one half the value for the sample 3 ingesting group (FIG. 7).

From the foregoing, it was suggested that unless sufficient emulsification was performed to prepare a stable emulsion, the amount of absorption should decrease, or no efficient absorption should be obtained.

Example 5

Dispersion Test

Samples

One gram of sesamin (product of TAKEMOTO OIL & FAT Co., Ltd.; sesamin/episesamin=51.1:48.2) was suspended in 50 g of middle-chain fatty acid triglyceride (MCT) (ACTOR M-1; product of RIKEN VITAMIN CO., LTD.) or 50 g of olive oil, each having been heated to 100° C., and the suspensions were agitated for 20 minutes with a magnetic stirrer until the sesamin dissolved uniformly to prepare an oil phase. In a separate step, 0-100 g of enzyme-decomposed lecithin (SUN LECITHIN VA-1; product of Taiyo Kagaku Co., Ltd.; 33.3% active ingredient; obtained from soybean) as a surfactant was mixed and dissolved in water that had been heated to 80° C., whereby 1000 g of a water phase was prepared. The previously prepared oil phase was cooled to about 80° C., poured while being agitated into the water phase, and the mixture was subjected to pre-emulsification. For pre-emulsification, CLEAR MIX CLM-1.5S (product of M Technique) was used and agitation was performed at 5000 rpm for 5 minutes. In addition, as shown in Table 2, some of the samples were processed by main emulsification treatment following the pre-emulsification. In the main emulsification treatment, the pre-emulsified liquid was processed for 30 minutes at 80° C. with CLEAR MIX W-Motion CLM-2.2/3.7W (product of M Technique) with the rotor part running at 20000 rpm and the screen part at 12500 rpm. Consequently, under these various conditions, 16 kinds of sesamin-containing, water-soluble emulsified compositions (sesamin-containing, oil-in-water emulsions) were obtained (samples A-P). The average particle sizes of the oil droplets in those emulsions were measured with the dynamic light scattering particle size distribution analyzer Model LB-550 of HORIBA, Ltd. as in Example 1. Furthermore, 10 mL of each emulsion was metered in a centrifugal settling tube, allowed to stand at room temperature for 2 days, and visually checked for the state of segregation (dispersion stability).

TABLE 2

|  |  | Sample A | Sample B | Sample C | Sample D | Sample E | Sample F | Sample G | Sample H |
|---|---|---|---|---|---|---|---|---|---|
| Oil phase | Sesamin | | | | 1 g | | | | |
| | MCT | | | | 50 g | | | | |
| Water Phase | Water | 1000 g | | 975 g | | 950 g | | 925 g | 900 g |
| | Surfactant | 0 g | | 25 g | | 50 g | | 75 g | 100 g |
| With(○) or without(X) of main emulsification | | ○ | X | ○ | X | ○ | X | X | X |

|  |  | Sample I | Sample J | Sample K | Sample L | Sample M | Sample N | Sample O | Sample P |
|---|---|---|---|---|---|---|---|---|---|
| Oil phase | Sesamin | | | | 1 g | | | | |
| | Olive oil | | | | 50 g | | | | |
| Water Phase | Water | 1000 g | | 975 g | | 950 g | | 925 g | 900 g |
| | Surfactant | 0 g | | 25 g | | 50 g | | 75 g | 100 g |
| With(○) or without(X) of main emulsification | | ○ | X | ○ | X | ○ | X | X | X |

The results are shown in Table 3. When MCT was used as oil or fat, the average particle size was smaller than when olive oil was used. In addition, it was suggested that particles smaller than 300 nm would show superior dispersion stability.

TABLE 3

|  | Sample A | Sample B | Sample C | Sample D | Sample E | Sample F | Sample G | Sample H |
|---|---|---|---|---|---|---|---|---|
| Average particle size (nm) | 277.7 | 2454.9 | 81.5 | 514.9 | 95.9 | 429.8 | 329.8 | 469.2 |
| Dispersion stability No segregation occurred: ○ Segregation occurred: X | ○ | X | ○ | X | ○ | X | X | X |

|  | Sample I | Sample J | Sample K | Sample L | Sample M | Sample N | Sample O | Sample P |
|---|---|---|---|---|---|---|---|---|
| Average particle size (nm) | 862.3 | 1590.9 | 157.3 | 3313.7 | 172.9 | 2788.0 | 2985.4 | 2819.7 |
| Dispersion stability No segregation occurred: ○ Segregation occurred: X | X | X | ○ | X | ○ | X | X | X |

Example 6

Soft Gel

| (Oil phase) | |
|---|---|
| Sesamin | 3.5 g |
| Vitamin E (α-tocopherol content 50%) | 40 g |
| Wheat germ oil | 160 g |

| (Water phase) | |
|---|---|
| Water | 1000 g |
| Enzyme-decomposed lecithin | 25 g |

As in Example 1, an oil phase and a water phase were prepared and by adding the oil phase dropwise to the water phase, an oil-in-water composition was prepared. This composition was filled into soft capsules of gelatin shell (60.0% gelatin, 30.0% glycerin, 0.15% methyl paraoxybenzoate, 0.51% propyl paraoxybenzoate, and q.s. water) by the usual rotary process to prepare softgels.

Example 6

Health Drink

| Sesamin | 0.1% |
|---|---|
| Olive oil | 5% |
| Liquid sugar | 10% |
| Sour agent | 0.2% |
| Flavoring agent | 0.2% |
| Enzyme-decomposed lecithin | 1.5% |
| Water | 88.4% |

Sesamin was added to olive oil while heating until it dissolved to make a sesamin dissolving liquid. The prescribed amounts of liquid sugar, water and enzyme-decomposed lecithin were mixed and agitated at high speed, followed by the addition of the sour agent and flavoring agent to prepare a sesamin-containing health drink.

The invention claimed is:

1. An oil-in-water emulsion suitable for oral administration comprising a water phase and an oil phase emulsified in the water phase,
   wherein the oil phase comprises at least one kind of lignan-class compounds dissolved in the oil phase,
   wherein a ratio between lignin-class compound and the oil phase is about 1:15 to 100 by weight,
   wherein the lignan-class compound is sesamin and/or episesamin, and
   wherein oil droplets in the oil-in-water emulsion have an average particle size of 100 nm to 300 nm.

2. The oil-in-water emulsion according to claim 1, wherein the oil phase and/or water phase contains a surfactant in an amount effective for emulsification.

3. The oil-in-water emulsion according to claim 2, wherein the surfactant is lecithin or lysolecithin.

4. A food composition or an oral pharmaceutical composition comprising the oil-in-water emulsion according to claim 1.

5. A composition for oral administration comprising the water emulsion according to claim 1,
   wherein the oil-in-water emulsion comprises a water phase and an oil phase emulsified in the water phase, wherein the oil phase comprises at least one kind of lignan-class compounds dissolved in the oil phase,
   oil droplets in the oil-in-water emulsion have an average particle size of 100 nm to 300 nm,
   the oil-in-water emulsion optionally comprises a surfactant in an amount effective for emulsification, and
   the oil-in-water emulsion is effective in enabling the lignin-class compound to be absorbed at such a rate that the time to reach maximum blood concentration ($T_{max}$) is within 5 hours after oral administration.

6. The composition for oral administration according to claim 5, which comprises lecithin or lysolecithin as the surfactant.

7. A process for producing the oil-in-water emulsion according to claim 1, comprising the following steps:
   1) dissolving at least one of lignan-class compounds in oil or fat to prepare a lignin-class compound dissolving liquid which serves as an oil phase, wherein a ratio between lignan-class compound and the oil phase is about 1:15 to 100 by weight, and wherein the lignan-class compound is sesamin and/or episesamin;
   2) emulsifying the lignin-class compound dissolving liquid in a water phase to form an oil-in-water emulsion; and
   3) further emulsifying the lignan-class compound dissolving liquid until the oil droplets in the emulsion are reduced to an average particle size of 100 nm to 300 nm.

8. The process according to claim 7, wherein the step 2) is performed with a surfactant being added to the oil phase and/or water phase in an amount effective for emulsification.

9. The process according to claim 8, wherein the surfactant is lecithin or lysolecithin.

10. The oil-in-water emulsion according to claim 1, wherein the oil phase comprises fat or oil selected from the group consisting of almond oil, safflower oil, apricot kernel oil, avocado oil, evening primrose oil, wheat germ oil, corn oil, sunflower oil, walnut oil, olive oil, castor oil, kukui nut oil, grape seed oil, cocoa butter, coconut oil, soybean oil, rapeseed oil, peanut oil, rice oil, sesame oil, palm kernel oil, palm oil, jojoba oil, macadamia nut oil, shea butter, mango butter, kokum butter, whale oil, sardine oil, squid oil, margarine, and mixtures thereof.

11. The oil-in-water emulsion according to claim 1, wherein the oil phase comprises diacylglycerol, middle-chain fatty acid triglyceride (MCT), mixtures thereof.

* * * * *

UNITED STATES PATENT AND TRADEMARK OFFICE
CERTIFICATE OF CORRECTION

PATENT NO. : 8,685,455 B2  Page 1 of 1
APPLICATION NO. : 11/887074
DATED : April 1, 2014
INVENTOR(S) : Yamada et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 667 days.

Signed and Sealed this

Twenty-ninth Day of September, 2015

Michelle K. Lee
*Director of the United States Patent and Trademark Office*